United States Patent [19]
Thornton

[11] Patent Number: 5,263,491
[45] Date of Patent: Nov. 23, 1993

[54] AMBULATORY METABOLIC MONITOR

[76] Inventor: William Thornton, 701 Coward's Creek Rd., Friendswood, Tex. 77546

[21] Appl. No.: 883,424

[22] Filed: May 12, 1992

[51] Int. Cl.$^5$ .............................................. A61B 5/0205
[52] U.S. Cl. .................................. 128/774; 128/700; 128/670
[58] Field of Search ............... 128/670, 700, 774, 773, 128/782

[56] References Cited

U.S. PATENT DOCUMENTS

| | | | |
|---|---|---|---|
| 4,367,752 | 1/1983 | Jimenez | 128/782 |
| 4,757,453 | 7/1988 | Nasiff | 128/782 |
| 5,125,412 | 1/1992 | Thornton | 128/782 |

Primary Examiner—William E. Kamm
Assistant Examiner—Scott M. Getzow
Attorney, Agent, or Firm—Beecher, Keith D.

[57] ABSTRACT

An ambulatory metabolic monitoring system which includes a number of sensors which are adapted to be mounted on a subject for generating electric signals relating to various physical activities of the subject, and well as EKG signals, and signals indicative of the food and drink consumed by the subject, and which also includes a signal storage and processing unit which is carried by the subject and which is connected to the various sensors so that data related to the various physical activities and food and drink consumption of the subject may be stored and processed to provide information useful in monitoring the metabolic state of the subject.

12 Claims, 9 Drawing Sheets

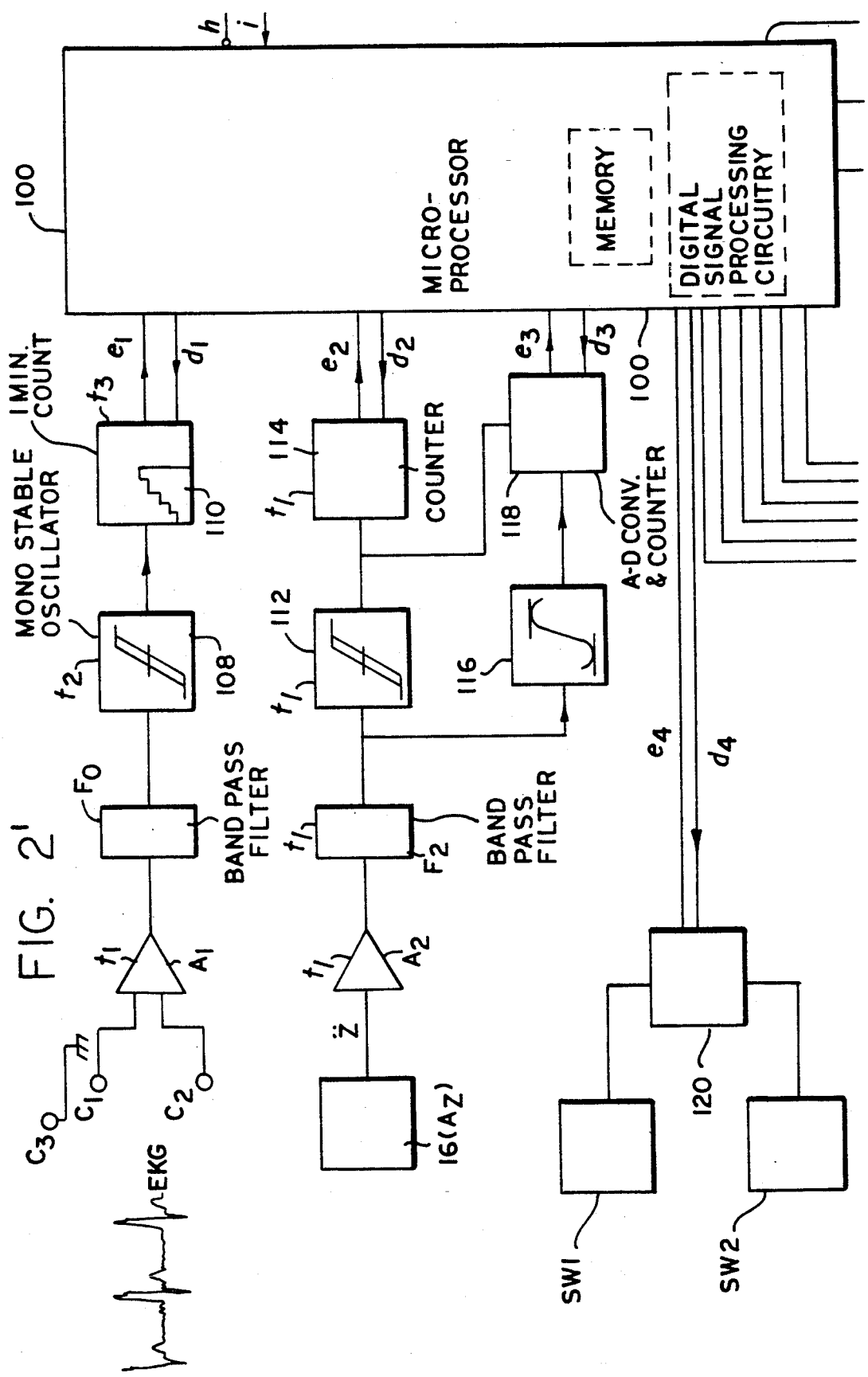

|  FOOD  |  |  | DRINK |  |
|---|---|---|---|---|
| MEAT | VEGS. |  | SOUPS | WATER |
| BREAD POTATOES PASTA | FRUIT |  | COFFEE TEA | SODA |
| SANDWICH | SWEETS |  | ALCOHOL BEER | MILK |
| SMALL | MED. |  | LARGE | ENTER |

FIG. 2A

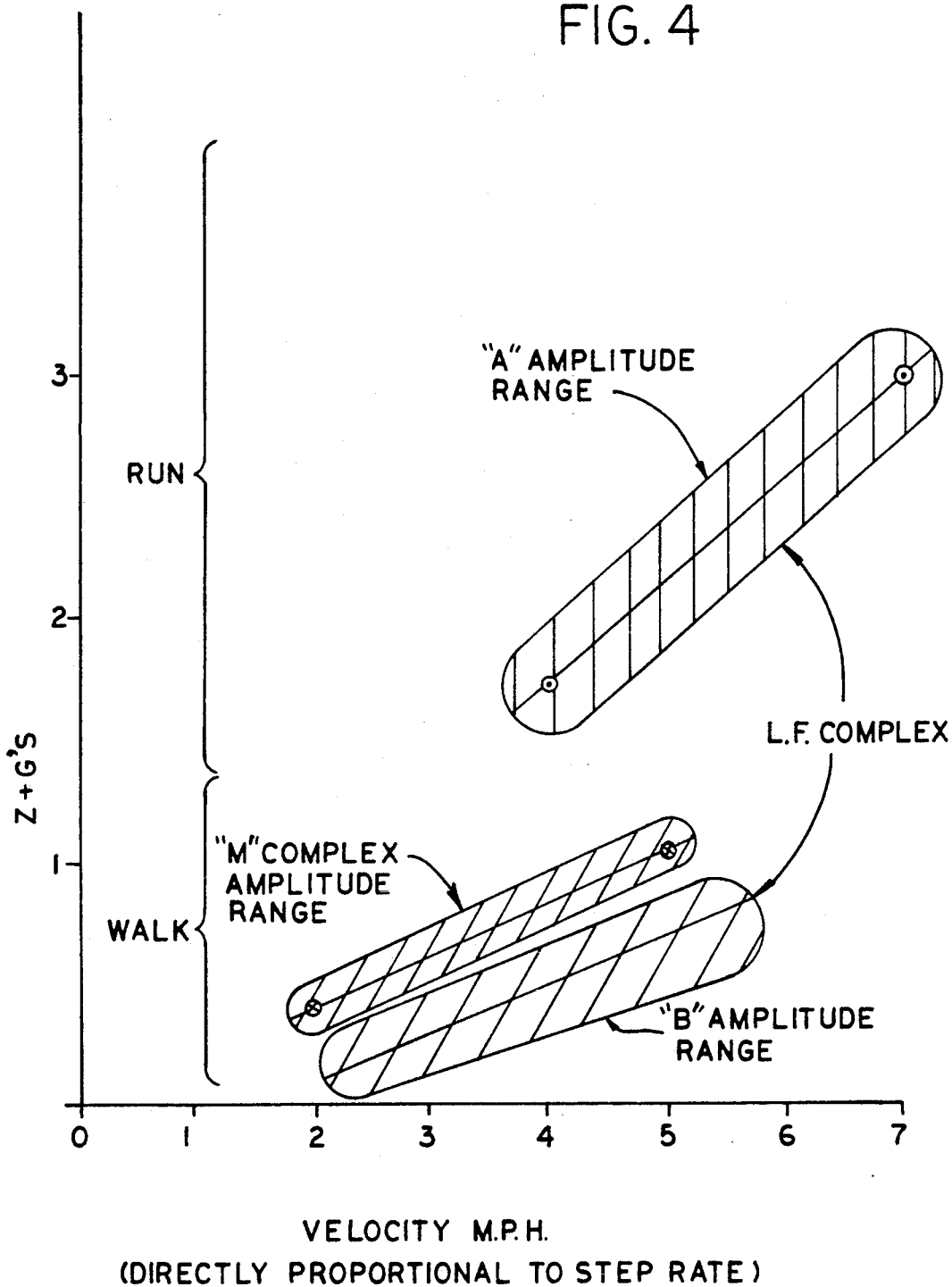

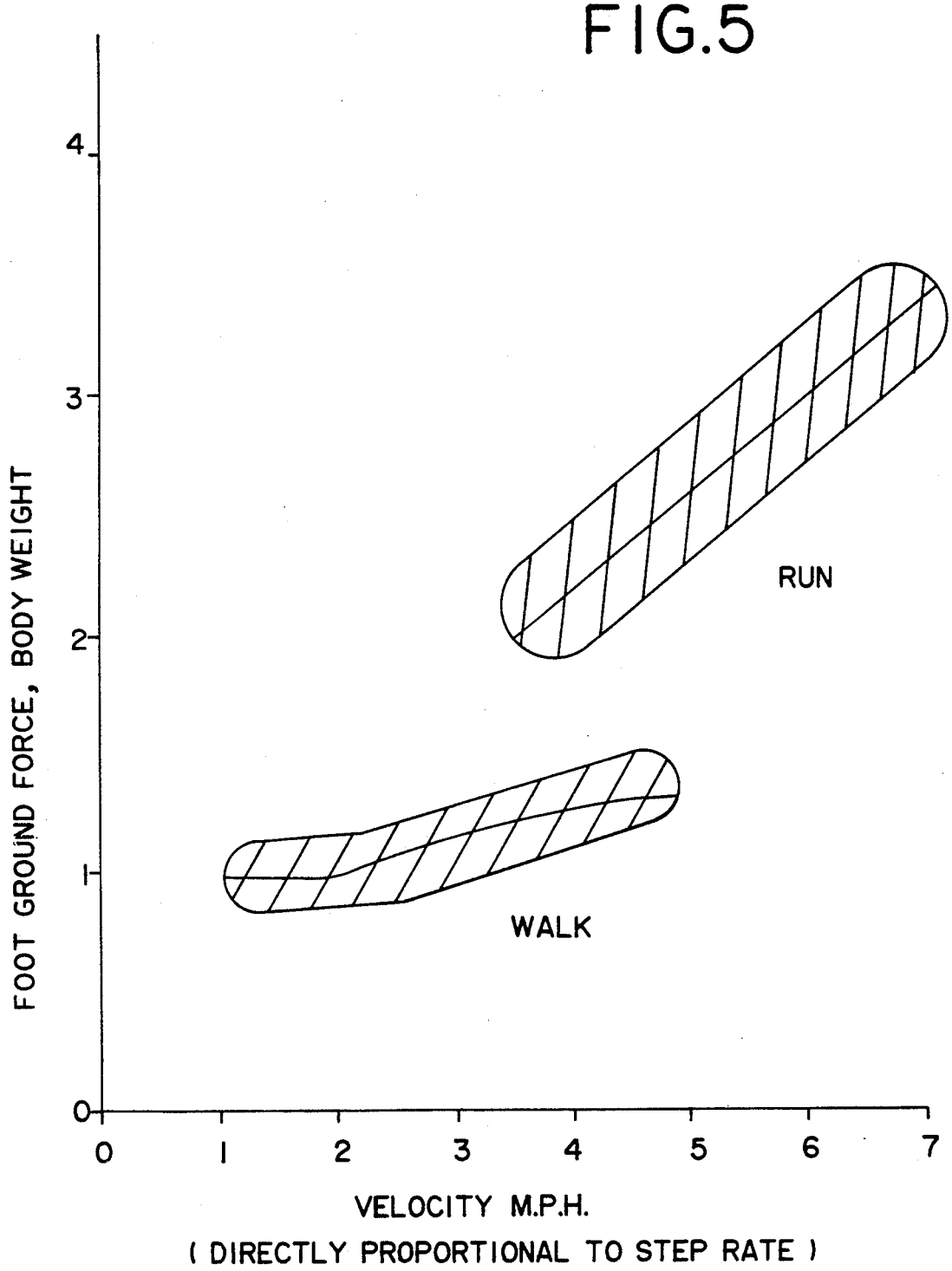

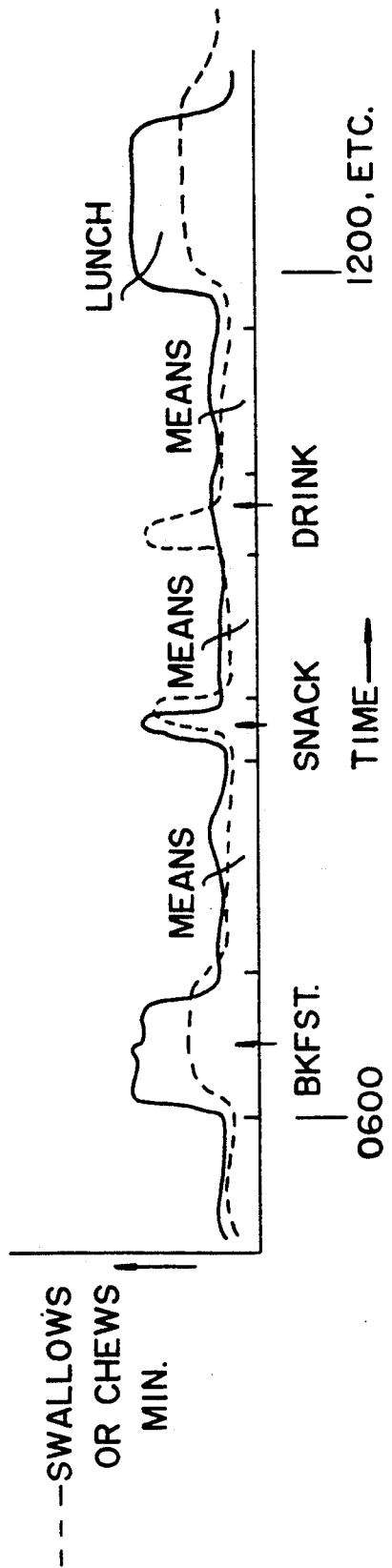

AMBULATORY METABOLIC MONITOR

BACKGROUND OF THE INVENTION

A major problem in the United States and in other developed countries today is metabolic imbalance, that is, excessive energy intake (eating) versus energy used (work and exercise). Billions of dollars are spent every year in trying to correct the situation, and for paying medical costs that result from the imbalance. Currently, while most of the imbalance appears to accrue from simple overindulgence, the question of relative efficiency remains unanswered. For example, questions as to why some individuals become fat on normal diets. A major cause why these and many other fundamental questions go unanswered is the lack of an appropriate means for studying the problems.

Records kept by the individuals as to their activities and food intake over periods of time are notoriously unreliable, and this has even given rise to the creation of elaborate expensive laboratories to make objective studies of the activities of relatively few individuals under artificial conditions.

U.S Pat. No. 4,830,021, which issued May 16, 1989; and application Ser. No. 554,549, filed Jul. 19, 1990, and which issued Jan. 14, 1992, as U.S. Pat. No. 5,080,105; Ser. No. 554,421, filed Jul. 19, 1990 and which issued Aug. 6, 1991, as U.S. Pat. No. 5,036,856; and Ser. No. 555,307, filed July 20, 1990 and which issued Feb. 19, 1991, as U.S. Pat. No. 4,993,421, all in the name of the present inventor, are directed to monitoring systems in which various physical activities of a subject are monitored along with indications of the emotional state of the subject, and by which certain ambient conditions are also monitored, to determine what effect if any, the physical activities and the emotional state of the subject have on abnormalities in the subject's EKG. Application Ser. No. 556,305, filed Jul. 23, 1990, now abandoned in the name of the present inventor provides a system for monitoring and quantitating musculoskeletal activity of a subject for use in orthopedic and other studies.

By modifications and by adding features to the various monitoring systems disclosed and claimed in the aforesaid patents, the ambulatory metabolic monitoring system of the present invention provides a new and unique capacity for recording energy expenditure and estimating energy intake for both investigation and practical treatment of these problems.

In a majority of individuals, locomotor activity consumes the largest amount of energy. Estimates of such energy consumption due to locomotor activity may be approximated from step rate alone, as described in Co-pending application Ser. No. 07/697,341, which was filed May 9, 1991, in the name of the present inventor as a continuation-in-part of the above-mentioned application Ser. No. 556,305 and which issued Jun. 30, 1992, as U.S. Pat. No. 5,125,412. Since only a characteristic signature in the 1–3 Hz range is required to count step rate, a single inexpensive accelerometer may be used. In addition, by adding foot ground force derivations, as also described in co-pending application Ser. No. 07/697,341, greater accuracy on energy expenditure may be obtained. Accuracy may be further refined by factoring in the heart rate of the individual. Other activities consume correspondingly less energy, for example, standing with occasional steps, standing quietly, seated activity, sitting, lying, lying asleep, and so on. The weight, sex and age of the patient should also be considered.

Estimation of the energy intake of the individual requires additional devices. One such device may be an ordinary digital diary which includes a push-button menu by which the individual may enter the types and quantities of food consumed. A second device is a sensor mounted on the subject which records chewing and swallowing activities, from which an estimation of intake may be derived, and which may be used to verify and augment the manually entered data.

Data from the sensors and devices referred to above may be processed to arrive at an estimation of the energy intake of a individual versus the energy consumed during the period.

Several monitoring systems will be described herein to fit varying needs of the operator. These needs may range, for example, from the researcher who requires as much information as possible, to the clinician who merely requires concise summaries regarding diet and exercise, and other specialists who require certain details for counseling and discussions with patients.

BRIEF DESCRIPTION OF THE DRAWINGS

FIGS. 2' and 2" together represent a block diagram of a solid state recorder which is carried by the subject and which is an important part of the invention;

FIG. 2A is a schematic representation of a keyboard which is carried by the subject, and which is connected to the recorder, so that the subject may enter into the recorder the types and quantities of food and drink consumed by the subject;

FIGS. 3A and 3B, 4 and 5 are curves which are useful in explaining the operation of the system of the invention;

FIG. 7, is a curve representing the typical food and drink ingestion activities of the subject over a period of time.

DETAILED DESCRIPTION OF THE ILLUSTRATED EMBODIMENT

Figure 1:
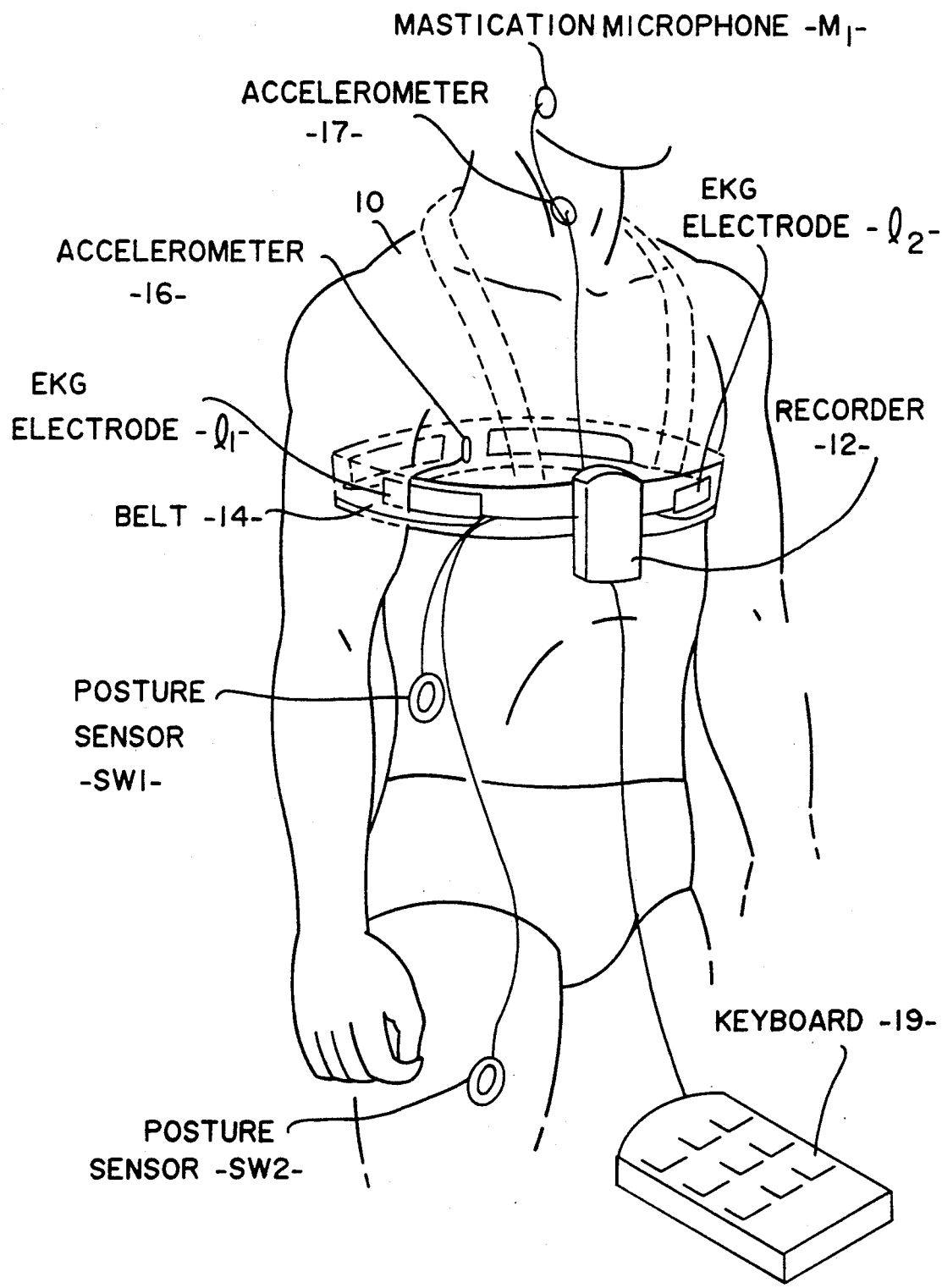
FIG. 1, is a representation of a subject on which various sensors and other instruments are mounted for carrying out the objectives of the present invention.

FIG. 1, is a representation of a subject 10, on which, as mentioned above, various sensors and other instruments are mounted for carrying out the desired metabolic monitoring functions of the system of the invention.

For example, a recorder 12 is carried by the subject on a belt 14, or by other means, Recorder 12, may be a solid state storage and processing unit, which will be described in some detail. An accelerometer 16 is also mounted on belt 14, the accelerometer being sensitive to vertical axis ($\dot{Z}$) accelerations ($\ddot{Z}$). A first position-sensitive switch SW1 is also carried by belt 14, and a second position-sensitive switch SW2 is mounted on the thigh of the subject. A miniature microphone M1 is adhesively mounted over the masseter (jaw) muscle of the subject 10. A second accelerometer 17 which is sensitive to movements of the subject in the X, Y plane is adhesively mounted over the subject's larynx.

Swallowing and torso activity are detected by the accelerometer 17, which, as stated, is adhesively attached to the skin of the subject over the larynx. Swallowing produces a large bi-phasic signal in accelerometer 17, while motion of the body and torso, which can also accrue in locomotion or in seated manual activities, produces slower, smaller amplitude signals. Hall effect or gravity dependent sensors may be used in the place of the accelerometer. Less expensive and simpler, in theory, are elastic strain gages placed over the jaw and larynx which are sensitive only to local motion Piezoelestic films may also be used.

A keyboard 19 (FIG. 2A) is connected to the recorder 12 for entering descriptions and quantities of foods and drinks consumed by the subject. The keyboard is shown schematically in FIG. 2A, and it may take the form of any appropriate miniature keyboard available on the market. As shown in the schematic representation of FIG. 2A, half the keyboard may have keys related to food, and the other half may have keys related to drink. The subject, by pressing the appropriately labeled keys, can enter signals into recorder 12 identifying the various foods and drinks that have been consumed, and also whether the quantities were "small", "medium" or "large". As indicated by the dotted line, the keyboard may be folded when not in use and carried, for example, in the subject's pocket. In accordance with known practice, the keys of the keyboard are inoperative when the keyboard is folded.

The keyboard 19 represents one possible means for entering signals representing ingestion activities of the subject into the system. For more exact studies, for example, appropriate means would be provided to enter signals representing more accurately measured volumes or masses of food and drink ingested by the patient would be provided, as well as a more detailed analyses of the ingested food.

Figure 2:
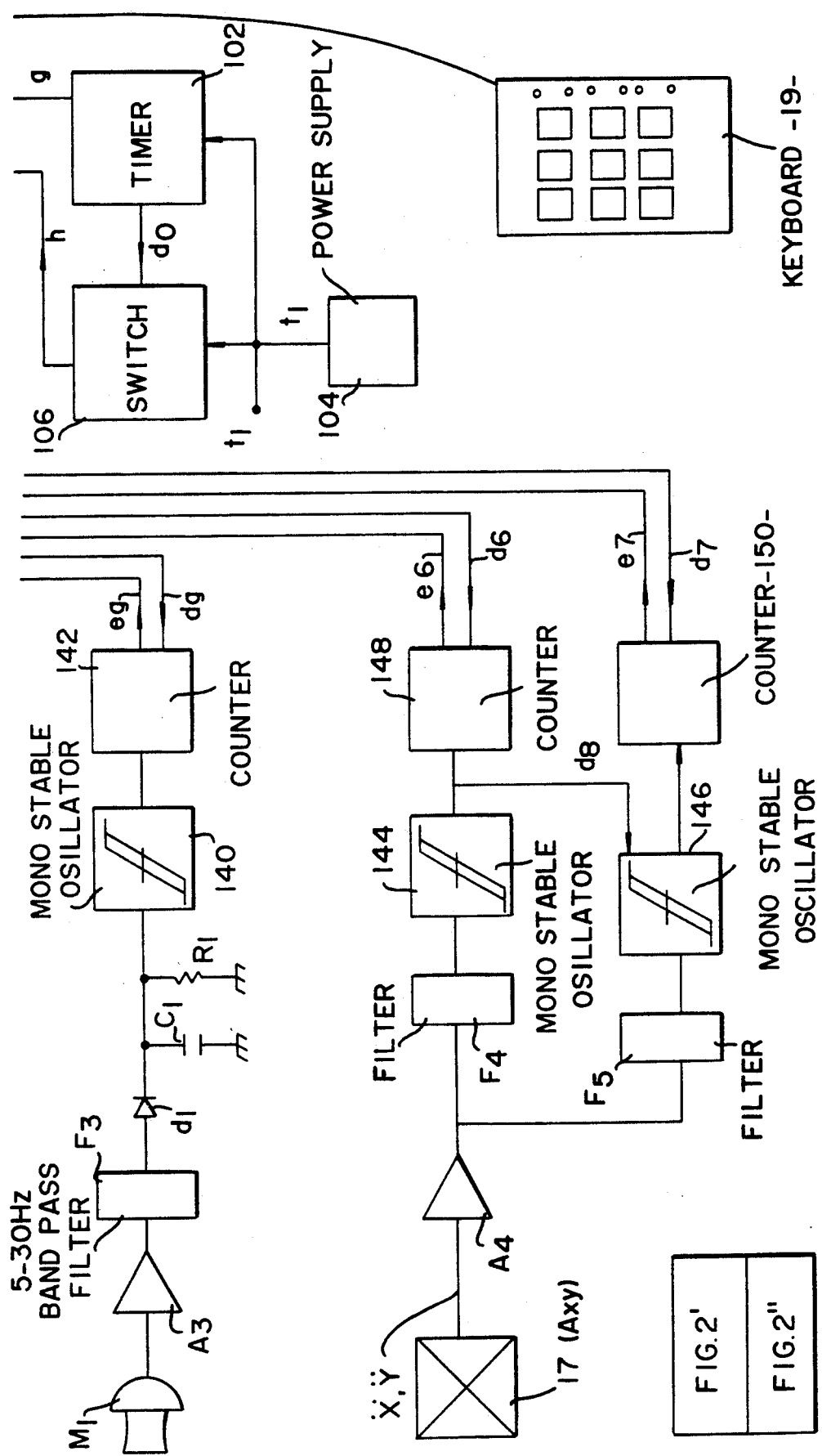
FIG. 2 is a block diagram which shows the relationship between FIGS. 2' and 2"

FIGS. 2' and 2" together represent a block diagram of the components of the solid state recorder 12. The recorder includes a microprocessor 100 which, in turn, includes a memory in which data fed into the recorder is stored, and digital signal processing circuitry. The recorder 12 also includes a timer 102 and a power supply 104. A switch 106 is included in the circuit of the power supply 104, and timer 102.

As shown in FIG. 2', recorder 12 receives signals from the accelerometer 16 from switches SW1 and SW2, as well as EKG signals from electrodes C1 and C2 which, as shown in FIG. 1, are also mounted on the subject. The recorder 12 also receives signals from microphone M1, from accelerometer 17, and from keyboard 19.

As described in co-pending application Ser. No. 697,341 which issued Jun. 30, 1992, as U.S. Pat. No. 5,125,412, the EKG signals from electrodes C1 and C2 are introduced through an amplifier A1 and a bandpass filter F0 (1-10 Hz), so that only the R Wave of the EKG signal is passed to trigger mono-stable oscillator 108. A small counter 110 (0-256 bits) counts the pulses from oscillator 108. The output of the counter is introduced to microprocessor 100 over lead e1 each time the counter is interrogated by an interrogate signal received from the microprocessor over lead d1. The interrogate signal also resets the counter to zero at the end of each minute, so that the microprocessor stores the count of the counter for each minute.

The acceleration signal ($\ddot{Z}$) from accelerometer 16 is introduced to an amplifier A2, and is passed through a bandpass filter F2 (1-10 Hz) to a mono-stable oscillator 112 (normal state zero). The output of the oscillator 112 is counted in a counter 114, and the count of that counter is likewise stored for each minute in the microprocessor 100 by way of lead e2, the counter being reset by an interrogate signal received from the microprocessor via lead d2. The output of bandpass filter F2 is also passed through a peak-to-peak detector circuit 116 to an analog-digital converter 118 which contains a digital memory such that peak-to-peak values for each step are added over a minute. That is, the acceleration is summed over each minute with the step rate. This memory feeds its output to the microprocessor by way of lead e3 and which is reset each minute by an interrogate or strobe signal received from the microprocessor over lead d3. The accelerometer 16 carried by the subject measures vertical accelerations ($\ddot{Z}$) of the subject at his center of gravity. The accelerometer is tightly coupled to the body of the subject by means, for example, of an elastic belt or adhesive means. The accelerations ($\ddot{Z}$) may be converted to vertical forces (Fz) in the microprocessor 100 in a manner fully described in U.S. Pat. No. 4,830,021, which issued in the name of the present inventor.

As shown in FIG. 2", accelerometer 17 is connected through an amplifier A4 to a pair of filters F4 and F5. Filter 4, is connected to a mono-stable oscillator 144, and filter F5 is connected to a mono-stable oscillator 146. Mono-stable oscillator 144 triggers counter 148 which is strobed each minute by a strobe signal received from microprocessor 100 over lead d6, and introduces its count at the end of each minute to the microprocessor over lead e6. Mono-stable oscillator 146 triggers counter 150, which, in turn, applies its count at the end of each minute to the microprocessor over a lead e7 in response to a strobe signal received over lead d7.

The position-sensor switches SW1 and SW2 are attached to the subject 10, one at his waist and the other at his thigh as described above. Switches SW1 and SW2, may be commercially available mercury gravity switches, or other appropriate gravity switches may be used. These switches serve to provide signals indicative of the posture of the subject, specifically whether the subject is standing, sitting or lying down. The operation of switches of SW1 and SW2 is described in detail in U.S. Pat. No. 4,830,021. The switches SW1 and SW2 are connected to a two digit state circuit 120, the output of which is applied to the microprocessor 100 over lead e4, and which is interrogated each minute by a strobe signal each minute received over lead d4.

Figure 3A:
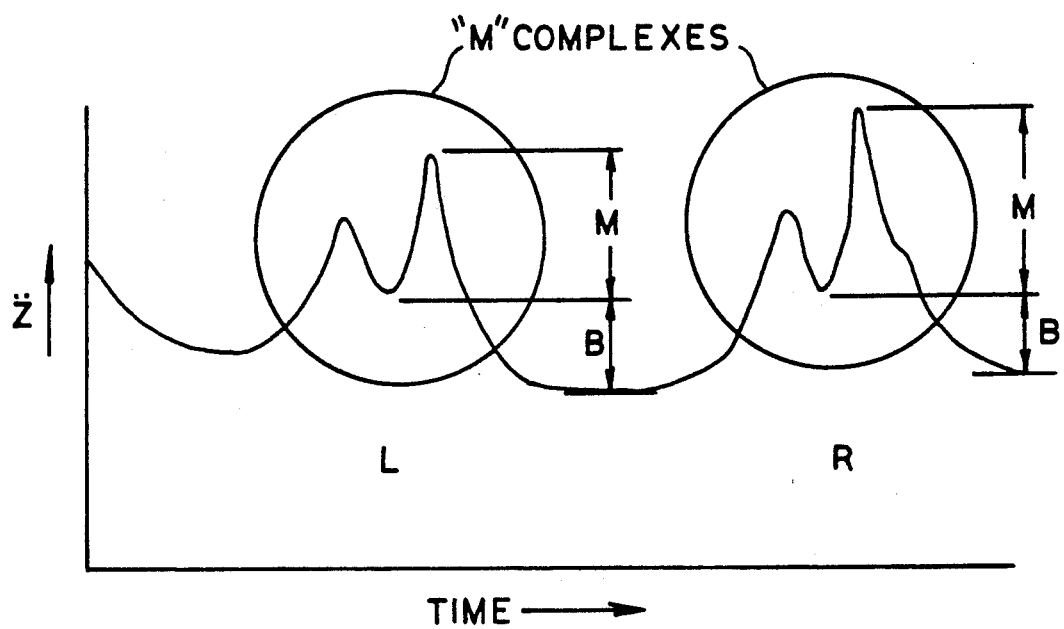

The vertical acceleration channel processes the acceleration signals ($\ddot{Z}$) in a manner which may be explained with reference to the waveforms of FIGS. 3A and 3B. FIG. 3A is the vertical acceleration ($\ddot{Z}$) waveform which occurs when the subject is walking, with L and R being foot strikes of the left and right feet. During the period when both feet are in ground contact, an "M" shaped wave complex of fairly high frequency components (for example, 8-15-Hz) is generated. This wave, as will be shown, is directly related to foot ground force (FGF). The signal also low frequency components B (0.5-3.0 Hz) which vary with step rate, but which are less well related to FGF during walking.

Figure 3B:
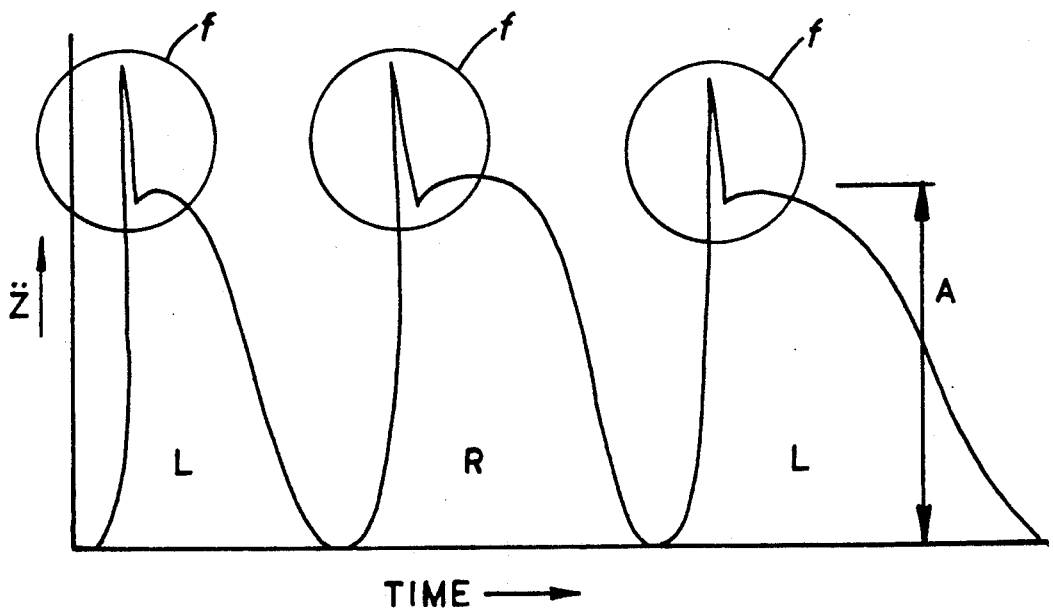

FIG. 3B is the vertical acceleration ($\ddot{Z}$) waveform during jogging/running, and includes low and high frequency components which are generated on each foot contact L, R, L, etc. The fast component f also lies in the 8-15 Hz region, but is unrelated to foot ground force (FGF) while the remaining low frequency (0.5-3 Hz) signal a is directly related to FGF. Step rate, FGF and mode (walk or jog/run) may be estimated as follows:

To measure step, fast components complexes are filtered by the bandwidth of 8-15 Hz by filter F2, and counted directly by counter 114. In actual practice a simpler scheme has been used. That is, simply to filter the low frequency component (0.5-3 Hz) of the ($\dot{Z}$) signal in bandpass filter F2, detect each step with an amplitude >0.3 G by circuit 2, and then count the complexes of the ($\dot{Z}$) signal which have an amplitude greater than a given level (e.g., ~0.3 G) for step rate.

Foot ground forces (FGF) may be derived from the ($\dot{Z}$) signal as follows: The high frequency "M" complex of walking, and the low frequency ($\dot{Z}$) complex of running are directly related to the ($\dot{Z}$) signal, as shown in FIG. 4, and can be approximated by filtering (5-18 Hz) the M complex and low frequency (L.F.) ($\dot{Z}$) complex (0.5-3 Hz) signals and peak detecting the signals separately and correcting for the relationship of FGF vs. velocity, as shown in FIGS. 4 and 5.

In practice, there is relatively little change in FGF over the normal range of walking, and it is simpler to estimate this value for walking by counting step rate and using a stored reference table or fixed proportional relationship during replay. Running FGF's are derived directly from the amplitude of the low frequency ($\dot{Z}$) complex, by the relation $FGF = K \cdot \dot{Z}$ where K is ~1.

Peak amplitude of walking and running low frequency complexes are both stored in the recorder of FIG. 2 in the following manner: After the accelerometer signal ($\dot{Z}$) from accelerometer 16 is amplified by A2, filtered by F2 (0.5-3 Hz) and amplitude detected by peak detector 116, its amplitude is digitized in the analog-to-digital converter 118 and summed for each minute by the converter. The output from the converter is transferred to storage in the microprocessor via lead e3 from a command received over lead d3 which also resets the converter 118 to zero.

The same low frequency complex ($\dot{Z}$) is filtered and used directly to count step rate in the recorder of FIG. 2, in the following manner: The mono-stable amplitude detector circuit 112 detects the peak-to-peak amplitude of every foot fall (step), and the step amplitudes are summed each minute by the 0-256 counter 114. The count of the counter is transferred to storage in the microprocessor 100 each minute over lead e2, as the counter is interrogated and reset by the interrogate signal received from the microprocessor over lead d2.

The body posture, such as lie, sit, stand is detected by the two-state position switches SW1 and SW2 of FIG. 1, as explained in the U.S. Pat. No. 4,830,021. As mentioned above, the two-state position switches SW1 and SW2 detect the times when the trunk and thigh are within horizontal or vertical limits. A conventional debounce circuit may be included to avoid vibration artifacts. The states of the contacts of the switches SW1 and SW2 are converted into one of the three states by a two digit state circuit 120 which introduces signals corresponding to the three posture positions to the microprocessor 100 over lead e4 as the circuit is interrogated by the interrogation signal received over lead d4. Accordingly, the predominant posture state of the subject for each minute is stored in the microprocessor 100. (In practice, the posture state is sampled several times a minute, and the predominant state is entered into memory.)

The power supply 104, timer 102, and switch 106, complete the recorder 12. The data stored each minute is time-tagged digitally by the timer 102 by timing signals introduced to the microprocessor over lead g. To save power, the microprocessor 100 is put in a power-down mode by switch 106 and line h2 for most of each minute, and is powered only during each brief sample period. This allows a single battery in power supply 104 to power the recorder for a week. Since locomotor habits vary greatly from day to day such long sample periods are necessary.

Additional data may be derived from the system of FIG. 1, including torso motion of the subject 10 (accelerometer 17), chewing and number of swallows of the subject (microphone M1 and accelerometer 17), and an estimate of food intake derived from keyboard 19. As shown in FIG. 2", microphone M1, is connected through an amplifier A3 and bandpass filter F3 (5-30 Hz) and through a diode D1 to a mono-stable oscillator 140. The diode is connected to a grounded capacitor C1 and a grounded resistor R1. The output of oscillator 140 is applied to a counter 142, and the count of the counter at the end of each minute is applied to microprocessor 100 over lead eg in response to strobe signals received over lead $d_g$.

The microphone M1, as mentioned above, and as shown in FIG. 1, is in contact with the skin which overlies the muscles of mastication of the subject 10. When the subject is chewing, high amplitude low frequency signals (3-16 Hz) are generated by the mastication muscles. Voice signals may also be present but their frequencies lie well above the filter cut off. Each cycle of mastication (chewing) products a burst of 3-16 Hz sound which is detected by the microphone $M_1$, amplifier $A_3$ and filter $F_1$ (5-30 Hz). This burst of sound is converted into a pulse shaped envelope by $d_1$, $C_1$, $R_1$ and level detected by the monostable oscillator 140 with suitable time hysteresis. These pulses are accumulated over each minutes' time by a counter 142 and transferred to the microprocessor memory by way of signal line $e_g$ and interrogate line $d_g$ each minute. The counter is also reset to zero by the interrogate line $d_g$.

The accelerator 17 is sensitive to motions in the horizontal plane (x-y), and its signals, x, y, are amplified by amplifier A4. The upper channel detects swallowing by bandpass filtering of the signals in bandpass filters F4, such that components in the 0.5-5.0 Hz range are passed, and voice signals are rejected. Mono-stable oscillator 144 forms a relatively high threshold detector, and it produces pulses for counter 148. All the swallows by the subject are summed for each minute in the counter and transferred to the microprocessor 100 by lead $e_6$, $d_6$ in the usual manner. A disabling signal generated by the swallowing channel is sent to the lower threshold detector 146 over lead d8 to avoid false counting by the torso motion channel.

The lower channel uses a lower frequency filter F5 to limit the signals passed to 0.5 Hz, and it also uses a lower threshold detector provided by mono-stable oscillator 146 to detect torso movements. These movements are counted by counter 150 for each minute, and supplied to the microprocessor over lead e7 in response to strobe signals received over lead d7.

The subject enters food estimates (general variety and quantity) into the microprocessor 100 by operation of keyboard 19, and signals representing such food estimates are time-tagged in the microprocessor and stored for replay.

Figure 6:
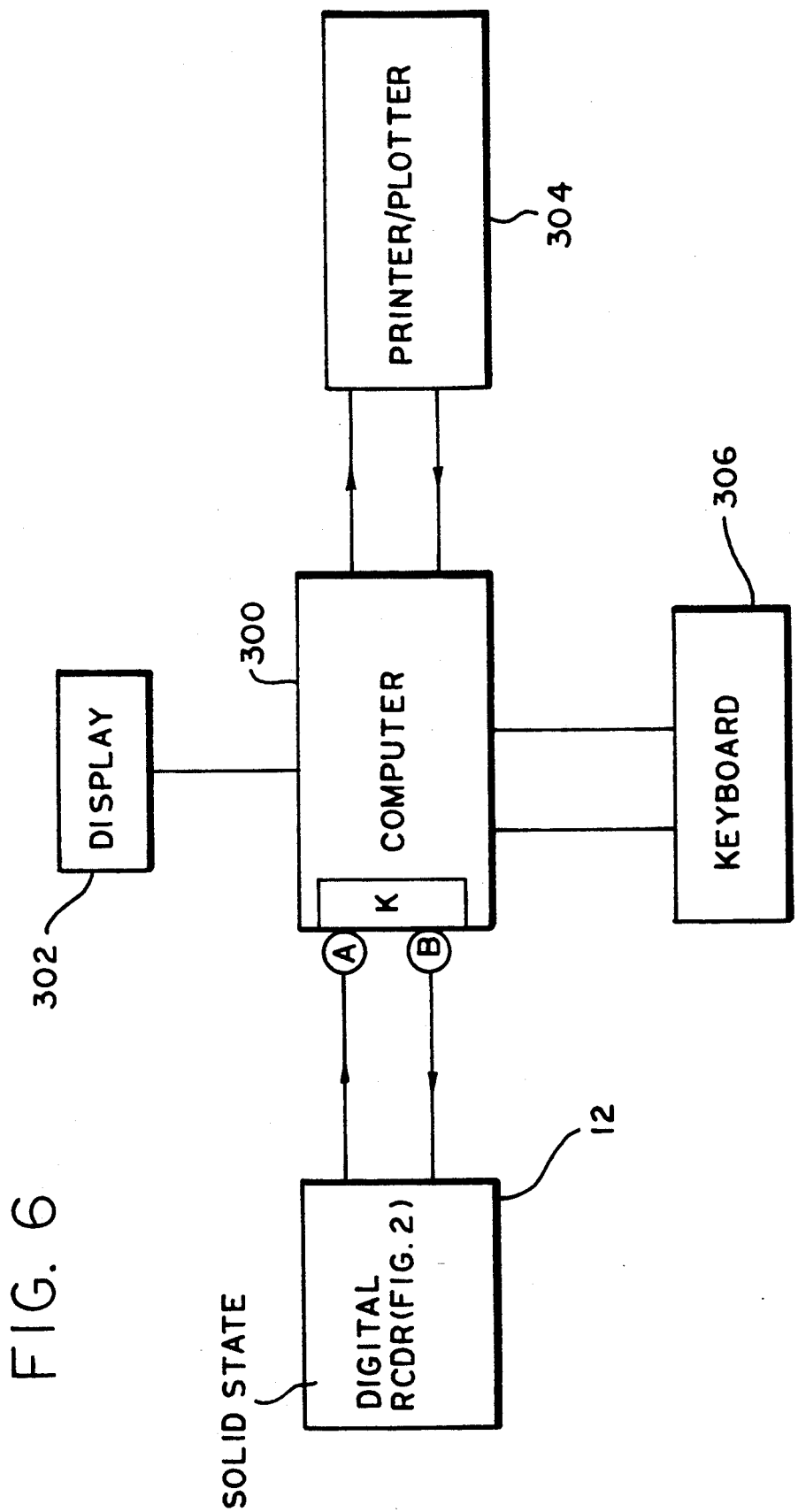
FIG. 6 is a block diagram of a computer and associated peripheral equipment which is used for the retrieval of data from the system of FIG. 2.

The next important feature of the system of the invention is data retrieval and processing. Data retrieval may be carried out by a computer 300 shown in FIGS. 6, and its associated peripheral units including, for example, a display 302, a printer-plotter 304, and keyboard 306. Basic data derived by the computer include: (a) time; (b) step rate over 1 minute; mean step rate par minute; (c) summed foot ground force (FGF); (d) mode (walk-/run); (e) posture; (f) postural transitions and (g) heart rate; (h) mastication cycle; (i) swallows; (j) torso motion. Of the above, a, b, c, e, g, h, i, and j are recorded directly. The data listed above, namely time, step rate, summed foot ground force, posture and heart rate, mastication cycles, swallows and torso motion are fed into the computer by interface circuit K and the data is stored in the computer. The remaining data are derived as follows:

(A) Foot Ground Force (FGF)

If the mode is "run", foot ground force (FGF) is derived in the computer from stored data in accordance with the following equation:

$$FGF = K \cdot \ddot{Z}$$

where: K is a proportionality constant near unity.

If the mode is "walk" then Foot Ground Force (FGF) is derived from a fixed look-up table stored in the computer as a function of step rate.

Such a table is given for example:

| Step Rate | Foot Ground Force |
|---|---|
| 50–100 | 1 B.W. |
| 100–110 | 1.1 B.W. |
| 110–120 | 1.2 B.W. |
| 120–130 | 1.3 B.W. |
| 130+ | 1.35 B.W. | where B.W. = Body Weight where B.W. = Body Weight

It should be noted that step rate is almost linearly related to speed in the walk mode, as designated in FIGS. 4 and 5. If the mode is jog/run, then referring to FIGS. 4 and 5, it should be noted that there is a large gap between the ($\ddot{Z}$) low frequency complexes in the walk mode as compared with the run mode. By derivation of the mean $\ddot{Z}$ amplitude of the stored signal, "mode" can be detected and used directly, in addition to being used as part of the Foot Ground Force algorithm.

(B) Posture and Heart Rate

Posture and heart rate are obtained directly from the stored signals.

(C) Postural Transition

Postural transitions are counted and identified when going from one state to another.

Display 302 and printer/plotter 304 may display and record the number of steps; step rate, mean, maximum, minimum for each mode (walk or jog/run); foot ground force—mean, maximum, minimum for each mode, plus the sum of the forces FGF x number of steps for each mode; posture-time spent in each posture, and the number of transitions from one posture to another; heart rate—mean, maximum, minimum.

The foregoing data is displayed and recorded over selected time periods within, for example, 24 hours. With the amount of data available, only typical guidelines for its use are set forth herein by way of examples. The processing breaks down into three logical areas: energy expenditure from activity; food/energy intake—subject estimate; ingestion activity and correlation with food/energy intake.

A unique feature of the system of the invention is the ability to cross correlate data and (a) drive new data, and (b) improve accuracy and put an estimate of accuracy on the data.

There are well established values of energy cost for virtually every activity. However, rather than trying to determine the specific activity, it is more appropriate to take classes of activity, as set forth below, and to assign values of energy costs and correct further for individual age, weight, sex and heart rate response. The class of activity and estimated costs for a 100 KGm subject are as follows:

| Activity | Criteria From Recorder (Time, Posture, H.R.,) | Energy Costs (KCAL. Min$^{-1}$) |
|---|---|---|
| Sleeping | (( ), ( ), ( )) | 1.8 |
| Lying awake | " | 2.0 |
| sitting, asleep | " | 2.1 |
| sitting quietly | " | 2.2 |
| sitting, active I | " | 3.1 |
| sitting, active II | " | 5.0 |
| standing, quietly | " | 3.4 |
| standing, active I | " | 6.0 |
| standing, active II | " | 10.0 |
| Walk, (slow to fast) | ( ), H.R., Posture | 8–13+ |
| Jog/Run (slow to fast) | ( ), H.R., Posture | 13–70 |

By summing the totals of the product of time and metabolic rates, a total expenditure is calculated. By taking average values for the foods and quantities consumed by the subject, a total summary of estimated caloric intake of may be obtained. By time-tagging, meals and extra meal intake can be obtained. It should be noted that such data is notoriously unreliable, and the ingestion criteria below is used for correlation/verification. For ingestion activity, since both jaw (chewing) and swallowing activity have individual base line activity, these levels will be established by having a computer take means when excess activity is not present. (See FIG. 7). By detecting significant increases by mean background chewing associated with swallowing makes a high probability of eating solid food likely while "excess" swallowing alone gives a probability of drinking. Such objective records can establish eating and drinking patterns which may then be used to correlate with the subject record.

There may be cases where less information is desired. For example, when only physical activity, or only intake, is being monitored, or where cheaper instrumentation is wanted and functions could be altered, and simplified accordingly. This is especially pertinent in software processing.

Except for research purposes which might want graphics or more digital details, relatively simple reporting would occur. It should be noted that as part of the patient identification system, weight, age and sex would be concluded, included in part of the computer data input, and weight especially would be used in processing.

The invention provides, therefore, an improved monitoring system for deriving data relating to the activity of a subject and which is useful for relating such activity to a study of the metabolic condition of the subject.

It will be appreciated that while a particular embodiment of the invention has been shown and described, modifications may be made. It is intended in the claims to cover all such modifications which come within the true spirit and scope of the invention.

I claim:

1. An ambulatory metabolic monitoring system comprising: microphone means to be mounted on a subject over the muscles of mastication; a keyboard to be carried by the subject for entering descriptions of the types and quantities of foods and drink consumed by the subject; first sensor means to be mounted on the subject for generating acceleration signals ($\dot{Z}$) indicative of vertical motions of the subject; EKG sensor means to be mounted on the subject for generating EKG signals relating to the cardiovascular state of the subject; signal storage and processing means coupled to said sensor means and to said keyboard for storing and processing the accelerations signals ($\dot{Z}$) from said first sensor means for successive time periods, for storing and processing EKG signals from said KEG sensor means for said successive time periods, and for storing and processing signals from said microphone means and from said keyboard for said successive time periods; and computer means connected to said signal storage and processing means and responsive to output signals therefrom for producing data relating to the walking/running mode step rate and the food and drink intake and heart rate of the subject for each of said successive time periods.

2. The ambulatory metabolic monitoring system defined in claim 1, and which comprises second sensor means to be mounted on the subject over the larynx for measuring motions of the subject in the horizontal plane and for producing acceleration signals (X) and (Y) in response to such motions, and in which said second sensor means is connected to said storage and processing means to enable said storage and processing means to store said acceleration signals (X, Y) from said second sensor means.

3. The ambulatory metabolic monitoring system defined in claim 1, and which includes posture sensor means to be mounted on the subject for generating signals relating to the posture of the subject; and in which said posture sensor means is connected to said storage and processing means to enable said means to store signals from said posture sensor for said successive time periods.

4. The ambulatory metabolic monitoring system defined in claim 1, in which said signal storage and processing means includes a microprocessor which, in turn, includes a memory and signal processing circuitry.

5. The ambulatory metabolic monitoring system defined in claim 1, in which said computer means derives data relating to foot ground force of the subject, the heart rate of the subject, the number of steps and step rate of the subject, the food and drink consumed by the subject, the energy expenditure of the subject, and ingestion activity of the subject during each of said successive time periods.

6. The ambulatory metabolic monitoring system defined in claim 1, and which includes posture sensor means to be mounted on the subject for generating posture signals relating to the posture of the subject; and in which said storage and processing means stores said posture signals for said successive time periods, and in which said computer means produces additional data related to the posture and postural transitions of the subject.

7. The ambulatory metabolic monitoring system defined in claim 1, and which includes means for detecting physical manifestations of food/drink ingested by the subject to produce signals for providing a measure of validation for said input data.

8. The ambulatory metabolic monitoring system comprising: first means for generating first electronic signals representing food/drink ingested by a subject; second means for generating second electronic signals representing physical activities of the subject; and means for processing said first and second signals to produce data representative of the metabolic condition of the subject.

9. The ambulatory metabolic monitoring system defined in claim 8, in which said processing means provides output signals representing the metabolic costs of activity of the subject, and the metabolic values of ingested food/drink as combined with established normal ranges.

10. The ambulatory metabolic measuring system defined in claim 7 in which said processing means processes said first and second signals over predetermined time intervals.

11. An ambulatory metabolic monitoring system comprising: first sensor means to be mounted on a subject for generating signals indicative of physical activities of the subject; second sensor means to be mounted on the subject for generating signals indicative of the caloric intake of the subject; signals storage and processing means coupled to said first and second sensor means for storing the signals from said sensor means for successive time periods; and computer means connected to said storage and processing means and responsive to output signals therefrom to produce data related to the caloric intake and physical activities of the subject during said successive time periods, so as to determine the metabolic condition of the subject.

12. An ambulatory metabolic computer processing system including: means for deriving signals from a subject representative of certain physical activities of the subject over predetermined periods of time; means for deriving signals representative of the caloric intake of the subject over said predetermined periods of time; signal storage and processing means for storing said signals; and computer means connected to said storage and processing means and responsive to output signals therefrom to produce data for metabolic determinations.

* * * * *